Dec. 4, 1951 N. GRILLO Plant Pat. 1,049
HYBRID TEA ROSE PLANT
Filed Jan. 3, 1950
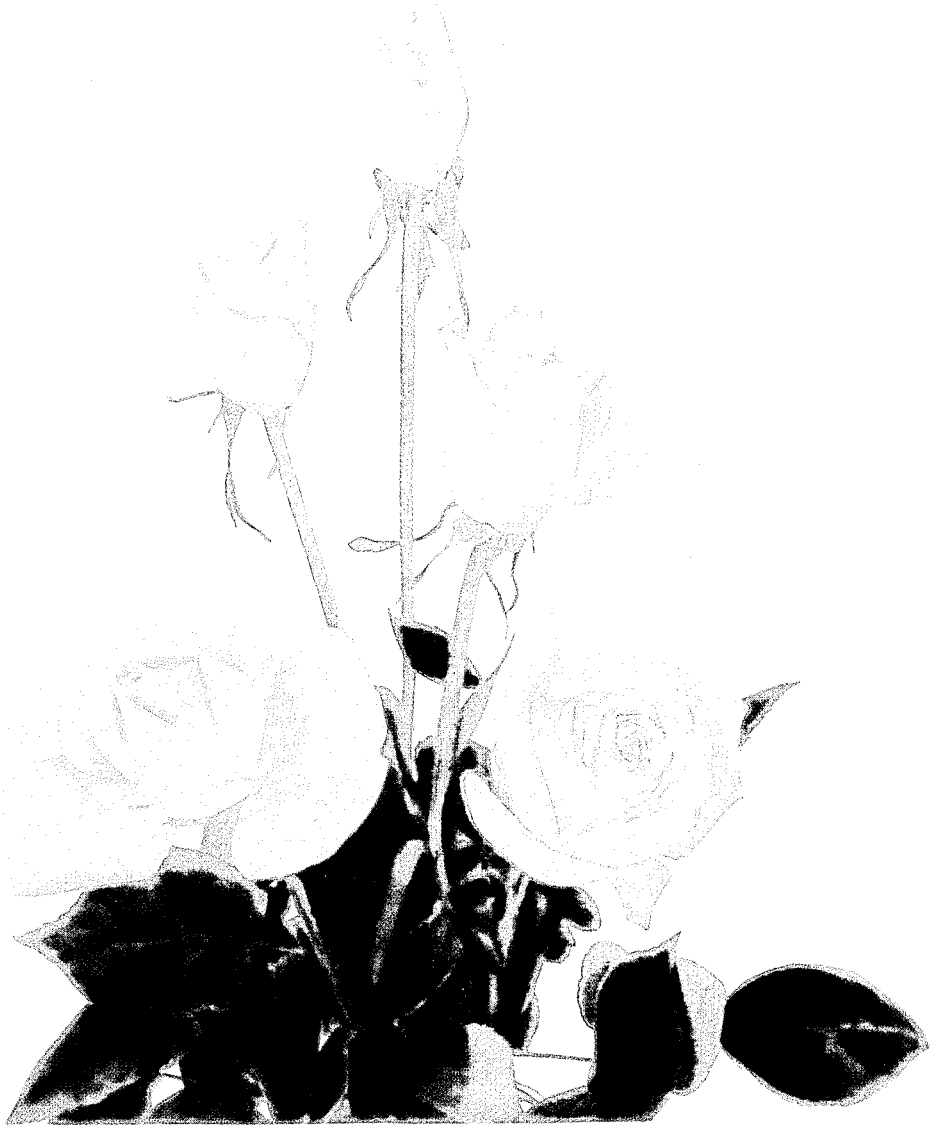
INVENTOR
Nicholas Grillo
By Orville M. Kile
Plant Pat. Agt.

Patented Dec. 4, 1951

Plant Pat. 1,049

UNITED STATES PATENT OFFICE 1,049

HYBRID TEA ROSE PLANT

Nicholas Grillo, Milldale, Conn.

Application January 3, 1950, Serial No. 136,457

1 Claim. (Cl. 47—61)

My present invention relates to an improvement in hybrid tea rose plants and consists of a new variety produced by crossing the known varieties Briarcliff (unpatented) and Regina Elena (Plant Patent No. 417), the latter itself having been a sport of Briarcliff. It produces flowers of the general color class of those of its parents, but the color is a darker, more uniform pink than either of the parents.

One of the most outstanding features of my new variety is the almost unfailing production of long, well-formed buds which open slowly and perfectly. Also notable is the strong plant growth and the prolific production of flowers.

The variety has been asexually reproduced by means of budding at my greenhouses at Milldale, Connecticut, and its characteristics appear to be permanent.

The illustrations accompanying these specifications show three buds and two partly-opened flowers of this new variety, together with portions of the stems and foliage. All are in as nearly their true colors as the artist could make them with the medium used.

In the following detailed description of my new variety, color terminology refers to Ridgway's Color Standards and Nomenclature except where it is obvious that the ordinary dictionary meaning of the term is intended.

*The plant*

Blooming habit: Very free-flowering; continuous, producing almost without fail all perfect well-shaped buds.

Growth: Upright bush. Very vigorous. Produces clean growth and an abundance of long, heavy stems.

Stems: Mostly smooth. Very strong, stiff, long, and bright green, approximately Light Cress Green (Plate XXXI). There are a few thorns which are relatively small, whitish-green and downward-pointing.

Foliage: Leaflets, 3 to 5.

*Quantity.*—Abundant.

*Size.*—Medium to large.

*Shape.*—Terminal leaflets are narrow elliptical with long-pointed acuminate apex. Lateral leaflets not quite so pointed.

*Color.*—Approximately Dark Dull Yellow Green (Plate XXXII).

*Texture.*—Heavy and leathery. Ribs prominent but veins almost indiscernible.

*Edge.*—At a distance edge appears to be smooth, but is finely and sharply serrated.

*Rachis.*—Extremely short, in many cases the leaflets and stipules coming together.

*Stipules.*—Medium size; clinging. Points are usually large and curved.

*The flower*

Bud:

*Size.*—Large.

*Form.*—Long, opening urnshape, with the first petal opening to make a wide bud, characteristic of the Briarcliff family.

*Color.*—Between Eosine Pink (Plate I) and Spinel Pink (Plate XXVI), with small light yellow aiglet which merges into the pink.

*Sepals.*—Long and at least two on each flower are foliaceous.

*Peduncle.*—Strong, smooth, straight, and heavy, holding flower upright. Color is same as that of the stems.

*Opening.*—Gradual and perfect.

Bloom:

*Borne.*—Singly on very strong stems.

*Size.*—Large, up to about 5 inches across when fully open.

*Form.*—Full and high-centered, retaining this form. When fully open, the petals stand apart from each other, making a full, loose form. The center usually remains covered until late stages.

*Fragrance.*—Moderate.

*Longevity.*—Has excellent lasting quality.

*Petalage*—From 45 to 50 petals.

*Color*—Vivid bright pink. The color would fall between Eosine Pink (Plate I) and Deep Rose Pink (Plate XII) although the flower has much more life and brilliance, especially in its depths. The general effect is that the color is uniformly spread throughout.

Petals:

*Size.*—Outer petals 1¾ to 2 inches in each direction.

*Shape.*—Approximately round. As the flower opens the petals roll back slightly, usually forming a central and two lateral points, making the petal rather shield-shaped.

*Texture.*—Substantial but not coarse or heavy.

*Appearance.*—Silky.

*Fragrance.*—Abundant.

*Persistence.*—Petals hold until dry.

Reproductive organs:

*Pistils.*—Many; very tightly bunched in center of flower. *Styles*—short; white. *Stigmas*—red, with slight green tip.

*Stamens.*—Relatively few; tightly surrounding pistils. *Filaments*—light yellow, approximately Empire Yellow (Pl. IV). Of various lengths but all rather short. *Anthers*—medium in size; dark yellow, approximately Light Cadmium (Pl. IV).

*Comparison*

The variety most like my new variety is its parent Briarcliff, but it differs from that variety principally in the following respects:

1. My new variety produces much stronger growth of plant.

2. The flower stems of my variety are much stronger and usually longer.

3. My variety is a more prolific producer of flowers.

4. My variety produces a larger bud and flower, which are more consistently well-shaped.

5. Color of the flower of my variety is darker yet more brilliant and more uniformly spread.

Having thus disclosed my invention, I claim:

The new and distinct variety of hybrid tea rose plant of the general Briarcliff type, substantially as herein shown and described, characterized particularly by its strong growth; long strong stems; prolific production of bloom; pointed, well-shaped buds; and brilliant pink color and large size of bud and flower.

NICHOLAS GRILLO.

No references cited.